United States Patent
Tokhtuev et al.

(10) Patent No.: US 9,140,648 B2
(45) Date of Patent: Sep. 22, 2015

(54) FLUOROMETER WITH MULTIPLE DETECTION CHANNELS

(71) Applicant: Ecolab USA Inc., Saint Paul, MN (US)

(72) Inventors: Eugene Tokhtuev, Duluth, MN (US); Christopher J. Owen, Duluth, MN (US); Anatoly Skirda, Hermantown, MN (US); Viktor Slobodyan, Duluth, MN (US); Paul Simon Schilling, Duluth, MN (US); William M. Christensen, Duluth, MN (US)

(73) Assignee: Ecolab USA Inc., Saint Paul, MN (US)

( * ) Notice: Subject to any disclaimer, the term of this patent is extended or adjusted under 35 U.S.C. 154(b) by 136 days.

(21) Appl. No.: 13/796,594

(22) Filed: Mar. 12, 2013

(65) Prior Publication Data
US 2014/0264077 A1    Sep. 18, 2014

(51) Int. Cl.
| | | |
|---|---|---|
| *G01T 1/10* | (2006.01) | |
| *G01J 1/58* | (2006.01) | |
| *G01N 21/59* | (2006.01) | |
| *G01N 21/64* | (2006.01) | |
| *G01N 21/85* | (2006.01) | |
| *G01N 21/53* | (2006.01) | |
| *G01N 21/17* | (2006.01) | |
| *G01N 21/84* | (2006.01) | |

(52) U.S. Cl.
CPC .............. *G01N 21/59* (2013.01); *G01N 21/645* (2013.01); *G01N 21/85* (2013.01); *G01N 21/53* (2013.01); *G01N 2021/1736* (2013.01); *G01N 2021/6491* (2013.01); *G01N 2021/8416* (2013.01)

(58) Field of Classification Search
CPC ....................... G01N 2021/6491; G01N 21/85
USPC ....................................... 250/458.1
See application file for complete search history.

(56) References Cited

U.S. PATENT DOCUMENTS

| | | | |
|---|---|---|---|
| 2,950,391 | A | 8/1960 | Brumley et al. |
| 3,264,474 | A | 8/1966 | Heiss |
| 3,754,145 | A | 8/1973 | Leaf |

(Continued)

FOREIGN PATENT DOCUMENTS

WO    2011121750 A1    10/2011

OTHER PUBLICATIONS

International Search Report and Written Opinion for International Application No. PCT/US2014/021197, mailed Jul. 1, 2014, 15 pages.

*Primary Examiner* — David Porta
*Assistant Examiner* — Jeremy S Valentiner
(74) *Attorney, Agent, or Firm* — Fredrikson & Byron, P.A.

(57) ABSTRACT

An optical sensor may have multiple detection channels to detect different characteristics of a fluid. For example, an optical sensor used in industrial cleaning and sanitizing applications may have multiple detection channels to detect when a system is both clean and properly sanitized. In one example, an optical sensor includes an optical emitter that directs light into a fluid, a first optical detector that detects light transmitted through the fluid, a second optical detector that detects light scattered by the fluid, and a third optical detector that detects fluorescent emissions emitted by the fluid. The optical emitter and optical detectors can be positioned around an optical analysis area. Depending on the application, the optical emitter may be positioned to direct light adjacent a wall of the optical analysis area rather than at a center of the optical analysis area, which may increase the strength of signal on the detection channels.

19 Claims, 7 Drawing Sheets

(56) References Cited

U.S. PATENT DOCUMENTS

| | | | |
|---|---|---|---|
| 3,763,374 A | 10/1973 | Tiffany et al. | |
| 3,901,656 A | 8/1975 | Durkos et al. | |
| 3,903,422 A | 9/1975 | Buhrer | |
| 4,008,397 A | 2/1977 | Zdrodowski | |
| 4,031,398 A | 6/1977 | Callis et al. | |
| 4,031,399 A | 6/1977 | Klein et al. | |
| 4,076,420 A * | 2/1978 | De Maeyer et al. | 356/73 |
| 4,117,338 A | 9/1978 | Adrion et al. | |
| 4,178,512 A | 12/1979 | Frungel et al. | |
| 4,293,225 A | 10/1981 | Wheaton et al. | |
| 4,501,970 A | 2/1985 | Nelson | |
| 4,643,877 A | 2/1987 | Opitz et al. | |
| 4,661,711 A | 4/1987 | Harjunmaa | |
| 4,691,110 A | 9/1987 | Nebe et al. | |
| 4,859,864 A * | 8/1989 | Smith | 250/577 |
| 4,877,965 A | 10/1989 | Dandliker et al. | |
| 5,061,076 A | 10/1991 | Hurley | |
| 5,094,531 A | 3/1992 | Garner et al. | |
| 5,221,958 A | 6/1993 | Bohnenkamp | |
| 5,323,008 A | 6/1994 | Studholme et al. | |
| RE34,782 E | 11/1994 | Dandliker et al. | |
| 5,422,719 A | 6/1995 | Goldstein | |
| 5,489,977 A * | 2/1996 | Winslow et al. | 356/73 |
| 6,013,034 A | 1/2000 | Fernandes Da Cunha Vaz et al. | |
| 6,121,053 A | 9/2000 | Kolber et al. | |
| 6,144,455 A | 11/2000 | Tuunanen et al. | |
| 6,252,657 B1 | 6/2001 | Bohnenkamp | |
| 6,313,471 B1 | 11/2001 | Giebeler et al. | |
| 6,369,894 B1 | 4/2002 | Rasimas et al. | |
| 6,563,585 B1 | 5/2003 | Rao et al. | |
| 6,670,617 B2 | 12/2003 | Banks | |
| 6,825,927 B2 | 11/2004 | Goldman et al. | |
| 6,830,731 B1 | 12/2004 | Buechler et al. | |
| 7,099,012 B1 | 8/2006 | Crawford et al. | |
| 7,186,989 B2 | 3/2007 | Farmer et al. | |
| 7,416,700 B2 | 8/2008 | Buechler et al. | |
| 7,416,701 B2 | 8/2008 | Tokhtuev et al. | |
| D580,285 S | 11/2008 | Hendrickson et al. | |
| 7,491,366 B2 | 2/2009 | Tokhtuev et al. | |
| 7,504,641 B2 | 3/2009 | Tuunanen et al. | |
| 7,550,746 B2 | 6/2009 | Tokhtuev et al. | |
| 7,567,347 B2 | 7/2009 | Aasmul | |
| 7,652,267 B2 | 1/2010 | Tokhtuev et al. | |
| 7,867,718 B2 | 1/2011 | Nilsson et al. | |
| 7,869,042 B2 | 1/2011 | Aasmul | |
| 7,920,260 B2 | 4/2011 | Mantele et al. | |
| 7,989,780 B2 | 8/2011 | Tokhtuev et al. | |
| 8,248,611 B2 | 8/2012 | Christensen et al. | |
| 8,269,193 B2 | 9/2012 | Christensen et al. | |
| 8,352,207 B2 | 1/2013 | Tokhtuev et al. | |
| 8,373,140 B2 | 2/2013 | Tokhtuev et al. | |
| 2003/0006385 A1 | 1/2003 | Banks | |
| 2003/0016352 A1 | 1/2003 | Goldman et al. | |
| 2003/0049175 A1 | 3/2003 | Buechler et al. | |
| 2003/0058450 A1 | 3/2003 | Mosley et al. | |
| 2003/0062485 A1 | 4/2003 | Fernandez et al. | |
| 2003/0142316 A1 * | 7/2003 | Schenkl et al. | 356/442 |
| 2004/0241047 A1 | 12/2004 | Buechler et al. | |
| 2005/0105080 A1 | 5/2005 | Landlinger | |
| 2005/0269522 A1 | 12/2005 | Farmer et al. | |
| 2006/0250606 A1 * | 11/2006 | Kaye et al. | 356/73 |
| 2006/0256330 A1 | 11/2006 | Leipertz | |
| 2006/0286676 A1 | 12/2006 | Van Camp et al. | |
| 2007/0153279 A1 | 7/2007 | Aasmul | |
| 2007/0200073 A1 | 8/2007 | Tuunanen | |
| 2008/0203332 A1 | 8/2008 | McStay et al. | |
| 2009/0212236 A1 * | 8/2009 | Tokhtuev et al. | 250/461.1 |
| 2009/0312616 A1 | 12/2009 | Paseman et al. | |
| 2010/0048730 A1 | 2/2010 | Li et al. | |
| 2010/0090126 A1 | 4/2010 | Aasmul | |
| 2010/0182606 A1 * | 7/2010 | Prenner et al. | 356/440 |
| 2011/0089341 A1 | 4/2011 | Aasmul | |
| 2011/0127444 A1 | 6/2011 | Ozasa et al. | |
| 2011/0240886 A1 | 10/2011 | Tokhtuev et al. | |
| 2011/0240887 A1 | 10/2011 | Christensen et al. | |
| 2011/0242539 A1 | 10/2011 | Christensen et al. | |

* cited by examiner

FLUOROMETER WITH MULTIPLE DETECTION CHANNELS

TECHNICAL FIELD

This disclosure relates to optical measuring devices and, more particularly, to fluorometers for monitoring the concentration of one or more substances in a sample.

BACKGROUND

In cleaning and antimicrobial operations, commercial users (e.g., restaurants, hotels, food and beverage plants, grocery stores, etc.) rely upon the concentration of a cleaning or antimicrobial product to make the product work effectively. Failure of a cleaning or antimicrobial product to work effectively (for example due to concentration issues) can cause a commercial user to perceive the product as lower quality. End consumers may also perceive the commercial provider of such products as providing inferior services. In addition, commercial users may be investigated and/or sanctioned by government regulatory and health agencies. Accordingly, there is a need for a system that can monitor the characteristics of fluid solutions, e.g., to determine if the concentration of a product is within a specified concentration range. The same may be true for other applications, such as water care, pest control, beverage and bottling operations, oil and gas refining and processing operations, and the like.

One method of monitoring the concentration of a product relies on monitoring the fluorescence of the product that occurs when the sample (and the product within the sample) is exposed to a predetermined wavelength of light. For example, compounds within the product or a fluorescent tracer added to the product may fluoresce when exposed to certain wavelengths of light. The concentration of the product can then be determined using a fluorometer that measures the fluorescence of the compounds and calculates the concentration of the chemical based on the measured fluorescence.

Fluorometric spectroscopy concerns the detection of fluorescent light emitted by a sample of interest. It involves using a beam of light, usually ultraviolet (UV) light, that excites the electrons in molecules of certain compounds in the sample and causes them to emit light (i.e., to "fluoresce"). There are several types of fluorometers for measuring emitted fluorescence. Fluorometers generally have of a source of excitation radiant energy and a detector with a signal processor and a readout device.

SUMMARY

In general, this disclosure is directed to fluorometric devices, systems, and techniques for monitoring fluid samples. A fluorometer according to the disclosure may include an optical emitter and multiple optical detectors to monitor different characteristics of the fluid sample. For example, the fluorometer may include an optical emitter that detects light passing from the optical emitter and through the fluid sample to determine the concentration of a non-fluorescing species in the fluid. The fluorometer may further include another optical detector that detects fluorescent emissions from the fluid sample to determine the concentration of a fluorescing species in the fluid. By configuring the fluorometer with multiple optical detectors, the fluorometer may monitor different characteristics of a fluid under analysis. For example, when used to monitor water samples from an industrial cleaning and sanitizing operation, the fluorometer may determine if the flushing water is both clean (e.g., sufficiently devoid of a product being flushed) and contains a sufficient amount of sanitizer.

Although the design of the fluorometer can vary, in some applications, the fluorometer includes an optical emitter that is offset relative to an optical analysis area through which fluid flows. The optical emitter may be offset so that light emitted from the optical emitter is directed adjacent a wall of the optical analysis area rather than at a center of the optical analysis area. Such an arrangement may help minimize the amount of light emitted by the optical emitter that is reflected, for example, due to fluid turbidity or wall surfaces in the optical analysis area. In turn, this configuration may increase the strength of signal provided by an optical detector detecting light from the optical analysis area.

In one example, an optical sensor is described that includes an optical emitter, a first optical detector, a second optical detector, and a third optical detector. The optical emitter is configured to direct light into a fluid sample. The first optical detector is configured to detect light emitted by the optical emitter and transmitted through the fluid sample. The second optical detector is configured to detect light emitted by the optical emitter and scattered by the fluid sample. The third optical detector is configured to detect fluorescent emissions emitted by the fluid sample in response to the light emitted by the optical emitter. According to the example, the optical sensor also includes an optical emission filter positioned between the optical emitter and the fluid sample, a first optical detection filter positioned between the first optical detector and the fluid sample, a second optical detection filter positioned between the second optical detector and the fluid sample, and a third optical detection filter positioned between the third optical detector and the fluid sample. The example further specifies that the optical emission filter, the first optical detection filter, and the second optical detection filter are each configured to filter out the same wavelengths of light so that substantially any light detected by the first optical detector and the second optical detector is light emitted from the optical emitter and passing through the fluid sample.

In another example, a method is described that includes emitting light into a fluid sample via an optical emitter. The example method also includes detecting light emitted from the optical emitter and transmitted through the fluid sample via a first optical detector, detecting light emitted from the optical emitter and scattered by the fluid sample via a second optical detector, and detecting fluorescent emissions emitted by the fluid sample in response to light emitted by the optical emitter via a third optical detector. The example method specifies that detecting light via the first optical detector and detecting light via the second optical detector further includes filtering the light so that substantially any light detected by the first optical detector and the second optical detector is light emitted from the optical emitter and passing into the fluid sample.

In another example, an optical sensor system is described that includes a housing that defines an optical analysis area through which a fluid sample travels for optical analysis. The housing includes an optical emitter assembly that carries an optical emitter configured to direct light into the fluid sample, a first optical emitter assembly that carries a first optical detector configured to detect light emitted by the optical emitter and transmitted through the fluid sample, a second optical emitter assembly that carries a second optical detector configured to detect light emitted by the optical emitter and scattered by the fluid sample, and a third optical emitter assembly that carries a third optical detector configured to detect fluorescent emissions emitted by the fluid sample in response to the light emitted by the optical emitter. The housing also includes an optical emitter window positioned between the optical emitter and the optical analysis area, a first optical detector window positioned between the first optical detector and the optical analysis area, a second optical detector window positioned between the second optical detector and the optical analysis area, and a third optical detector window positioned between the third optical detector and the optical analysis area. According to the example, the first optical detector window is positioned on an opposite side of the optical analysis area from the optical emitter window, the second optical detector window is positioned at an approximately 90 degree angle relative to the optical emitter window, and the third optical detector window is positioned on an opposite side of the optical analysis area from the second detector window.

The details of one or more examples are set forth in the accompanying drawings and the description below. Other features, objects, and advantages will be apparent from the description and drawings, and from the claims.

DETAILED DESCRIPTION

Figure 1:
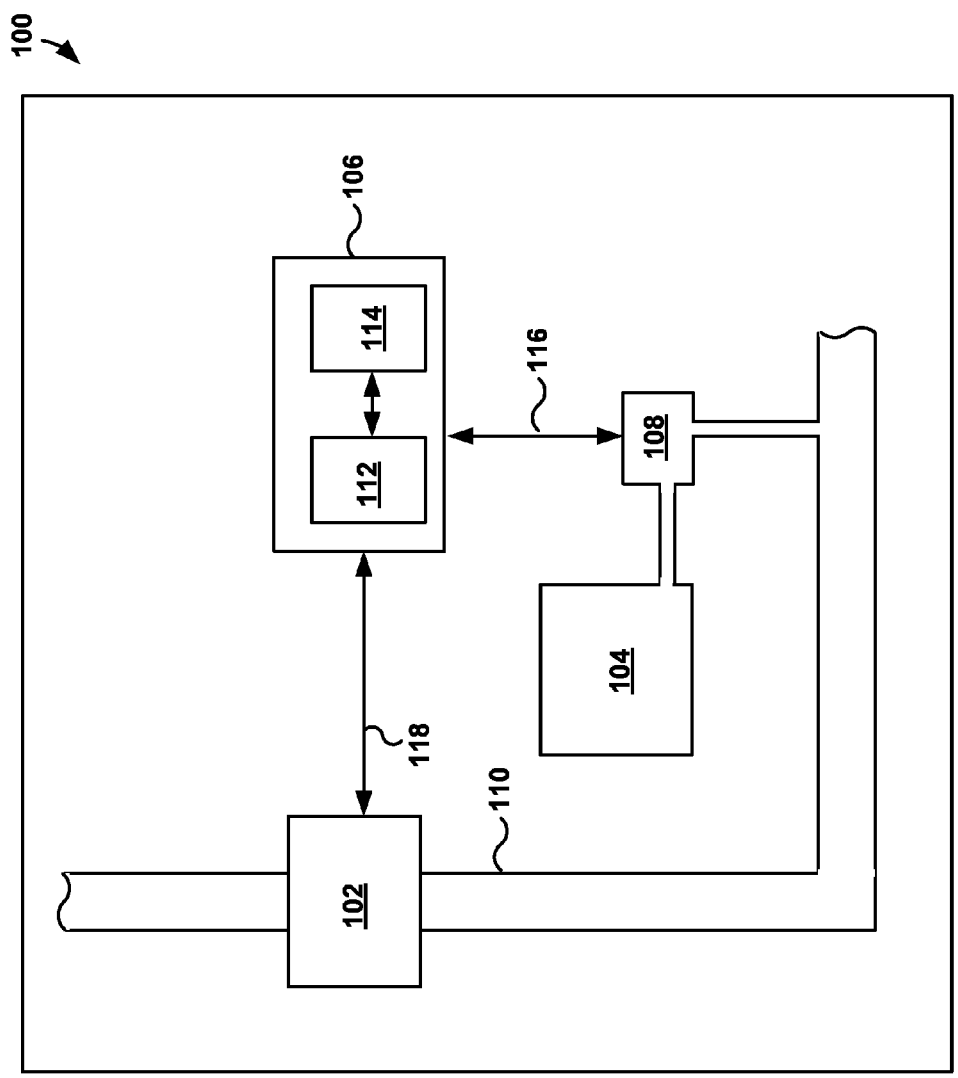
FIG. 1 is a diagram illustrating an example fluid system that includes an optical sensor according to examples of the disclosure.

The following detailed description is exemplary in nature and is not intended to limit the scope, applicability, or configuration of the invention in any way. Rather, the following description provides some practical illustrations for implementing examples of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Optical sensors are used in a variety of applications, including monitoring industrial processes. An optical sensor can be implemented as a portable, hand-held device that is used to periodically analyze the optical characteristics of a fluid in an industrial process. Alternatively, an optical sensor can be installed online to continuously analyze the optical characteristics of a fluid in an industrial process. In either case, the optical sensor may optically analyze the fluid sample and determine different characteristics of the fluid, such as the concentration of one or more chemical species in the fluid.

As one example, optical sensors are often used in industrial cleaning and sanitizing applications. During an industrial cleaning and sanitizing process, water is typically pumped through an industrial piping system to flush the piping system of product residing in pipes and any contamination build-up inside the pipes. The water may also contain a sanitizing agent that functions to sanitize and disinfect the piping system. The cleaning and sanitizing process can prepare the piping system to receive new product and/or a different product than was previously processed on the system.

An optical sensor can be used to monitor the characteristics of flushing and/or sanitizing water flowing through a piping system during an industrial cleaning and sanitizing process. Either continuously or on an intermittent basis, samples of water are extracted from the piping system and delivered to the optical sensor. Within the optical sensor, light is emitted into the water sample and used to evaluate the characteristics of the water sample. The optical sensor may determine whether residual product in the piping system has been sufficiently flushed out of the pipes, for example, by determining that there is little or no residual product in the water sample. The optical sensor may also determine the concentration of sanitizer in the water sample, for example, by measuring a fluorescent signal emitted by the sanitizer in response to the light emitted into the water sample. If it is determined that there is an insufficient amount of sanitizer in the water sample to properly sanitize the piping system, the amount of sanitizer is increased to ensure proper sanitizing of the system.

This disclosure describes an optical sensor that, in some examples, includes multiple optical detectors providing multiple optical detection channels. Each optical detector is positioned at a different location within the optical sensor relative to an optical emitter. For example, one optical detector may be positioned on an opposite side of a fluid channel from the optical emitter to detect light emitted by the optical emitter and transmitted through fluid within the fluid channel. Another optical detector may be positioned at a 90 degree angle relative to the optical emitter to detect light emitted by the optical emitter and scattered by fluid within the fluid channel. Yet another optical detector may be positioned at a different 90 degree angle relative to the optical emitter to detect light fluorescent emissions emitted by fluid within the fluid channel in response to light from the optical emitter.

By configuring the optical sensor with multiple optical detection channels, the optical sensor may comprehensively monitor fluid samples from an industrial process. For instance, when implemented as part of an online cleaning and sanitizing system, the optical sensor can receive fluid samples, such as samples of flushing water containing a sanitizing agent, and emit light into the fluid samples. The light detected by the different optical detectors of the optical sensor in response to the emitted light may then vary depending on the characteristics of the fluid sample. For example, a fluid sample obtained at the start of the cleaning process may contain a significant amount of optically opaque material (e.g., residual product in a piping system) so that neither the transmission detector nor the scattering detector receives any light. As fluid samples extracted from the system become progressively cleaner, the transmission detector may detect increasing amounts of light passing through the fluid sample until the transmission detector becomes saturated with light. Around this point in the cleaning process, however, the scattering detector may begin detecting light scattering within the fluid sample to allow continued monitoring of the fluid sample through the cleaning process. When the optical sensor further includes a detector that detects fluorescent emissions, the optical sensor can monitor the concentration of sanitization agent in the water samples. In this manner, the optical sensor can use the different optical detectors to monitor progress of a cleaning and sanitizing operation and the concentration of a sanitizing agent used in the cleaning and sanitizing operation. Of course, this is merely one example implementation of the optical sensor, and other implementations are both possible and contemplated.

While the optical sensor can have a variety of different configurations, in some examples, the optical sensor is designed to have an optical emitter that is offset from a center of a flow channel through which a fluid sample travels. For example, the optical emitter may be arranged to direct light adjacent to a wall of the flow channel rather than into a center of the flow channel. When so configured, the light emitted into the flow channel may be less likely to reflect off internal surfaces of the flow channel than when the light is directed into a center of the flow channel. In turn, this may increase the strength of the signal detected by the optical detectors, providing stronger signals for monitoring the characteristics of the fluid under analysis. In applications where fouling builds up on an optical detector during service, the ability to generate stronger signals can extend the length of time the optical sensor can remain in service between cleaning and maintenance.

Example optical sensor configurations will be described in greater detail below with respect to FIGS. 2-6. However, an example fluid system including an example optical sensor system will first be described with respect to FIG. 1.

FIG. 1 is a conceptual diagram illustrating an example fluid system 100, which may be used to produce a chemical solution having fluorescent properties, such as a sanitizer solution exhibiting fluorescent properties. Fluid system 100 includes optical sensor 102, a reservoir 104, a controller 106, and a pump 108. Reservoir 104 may store a concentrated chemical agent that can be blended with a diluent, such as water, to generate the chemical solution. Optical sensor 102 is optically connected to fluid pathway 110 and is configured to determine one or more characteristics of the solution traveling through the fluid pathway. In operation, optical sensor 102 can communicate with controller 106, and controller 106 can control fluid system 100 based on the fluid characteristic information generated by the optical sensor.

Controller 106 is communicatively connected to optical sensor 102 and pump 108. Controller 106 includes processor 112 and memory 114. Controller 106 communicates with pump 108 via a connection 116. Signals generated by optical sensor 102 are communicated to controller 106 via a wired or wireless connection, which in the example of FIG. 1 is illustrated as wired connection 118. Memory 109 stores software for running controller 106 and may also store data generated or received by processor 112, e.g., from optical sensor 102. Processor 112 runs software stored in memory 114 to manage the operation of fluid system 100.

As described in greater detail below, optical sensor 102 is configured to optically analyze a sample of fluid flowing through fluid pathway 110. In one example, optical sensor 102 includes an optical emitter that emits light into the fluid sample and multiple optical detectors (e.g., two, three, or more optical detectors) that measure light from the fluid sample. For example, optical sensor 102 may include an optical detector that is positioned to measure light emitted by the optical emitter and transmitted through the fluid sample. Optical sensor 102 may further include an optical detector that is positioned to measure light emitted by the optical emitter and scattered in a direction substantially orthogonal to the direction of emission. Optical sensor 102 may still further include an optical detector that is positioned and configured to measure fluorescent emissions emitted by the fluid sample. In operation, the optical detectors measuring light transmittance and scattering may be used to measure the optical transparency of the fluid sample, which may indicate the cleanliness of the system from which the fluid sample was extracted. The optical detector measuring fluorescence may be used to measure the concentration of a chemical species (e.g., sanitizer, corrosion control agent) in the fluid sample. By providing multiple optical detectors, optical sensor 102 may measure different optical characteristics of the fluid sample, such as the amount of optically opaque material in the fluid sample (for example, contamination being cleaned from a system) and a concentration of a chemical species in the fluid sample. In addition, the optical sensor 102 may measure the optical transparency of the fluid sample across a wide range of concentrations of the optically opaque material.

Independent of the number of optical detectors in optical sensor 102, in some additional examples described in greater detail below, that optical sensor has an optical emitter that is positioned to direct light adjacent to a wall of an optical analysis area rather than in a center of the optical analysis area. By moving the optical emitter so it is offset from a center of the optical analysis area, light emitted by the optical emitter may be less likely to reflect off internal surfaces in the optical analysis area. In turn, this may increase the amount of light received by an optical detector in optical sensor 102, increasing the strength of the signal produced by the optical detector.

In the example of FIG. 1, fluid system 100 is configured to generate a chemical solution having fluorescent properties. Fluid system 100 can combine one or more concentrated chemical agents stored within reservoir 104 with water or another diluting fluid to produce the chemical solutions. Example chemical solutions that may be produced by fluid system 100 include, but are not limited to, cleaning agents, sanitizing agents, cooling water for industrial cooling towers, biocides such as pesticides, anti-corrosion agents, anti-scaling agents, anti-fouling agents, laundry detergents, clean-in-place cleaners, floor coatings, vehicle care compositions, water care compositions, bottle washing compositions, and the like.

The chemical solutions generated by fluid system 100 may emit fluorescent radiation in response to optical energy directed into the solutions by optical sensor 102. Optical sensor 102 can then detect the emitted fluorescent radiation and determine various characteristics of the solution, such as a concentration of one or more chemical compounds in the solution, based on the magnitude of the emitted fluorescent radiation. In order to enable optical sensor 102 to detect fluorescent emissions, the fluid generated by fluid system 100 and received by optical sensor 102 may include a molecule that exhibits fluorescent characteristics. In some examples, the fluid includes a polycyclic compound and/or a benzene molecule that has one or more substituent electron donating groups such as, e.g., —OH, —NH$_2$, and —OCH$_3$, which may exhibit fluorescent characteristics. Depending on the application, these compounds may be naturally present in the chemical solutions generated by fluid system 100 because of the functional properties (e.g., cleaning and sanitizing properties) imparted to the solutions by the compounds.

In addition to or in lieu of a naturally fluorescing compound, the fluid generated by fluid system 100 and received by optical sensor 102 may include a fluorescent tracer (which may also be referred to as a fluorescent marker). The fluorescent tracer can be incorporated into the fluid specifically to impart fluorescing properties to the fluid. Example fluorescent tracer compounds include, but are not limited to, naphthalene disulfonate (NDSA), 2-naphthalenesulfonic acid, Acid Yellow 7,1,3,6,8-pyrenetetrasulfonic acid sodium salt, and fluorescein.

Independent of the specific composition of the fluid generated by fluid system 100, the system can generate fluid in any suitable fashion. Under the control of controller 106, pump 108 can mechanically pump a defined quantity of concentrated chemical agent out of reservoir 104 and combine the chemical agent with water to generate a liquid solution suitable for the intended application. Fluid pathway 110 can then convey the liquid solution to an intended discharge location. In some examples, fluid system 100 may generate a flow of liquid solution continuously for a period of time such as, e.g., a period of greater than 5 minutes, a period of greater than 30 minutes, or even a period of greater than 24 hours. Fluid system 100 may generate solution continuously in that the flow of solution passing through fluid pathway 110 may be substantially or entirely uninterrupted over the period of time.

In some examples, monitoring the characteristics of the fluid flowing through fluid pathway 110 can help ensure that the fluid is appropriately formulated for an intended downstream application. Monitoring the characteristics of the fluid flowing through fluid pathway 110 can also provide feedback information, e.g., for adjusting parameters used to generate new fluid solution. For these and other reasons, fluid system 100 can include a sensor to determine various characteristics of the fluid generated by the system.

In the example of FIG. 1, fluid system 100 includes optical sensor 102. Optical sensor 102 is configured to determine one or more characteristics of the fluid flowing through fluid pathway 110. Example characteristics include, but are not limited to, the concentration of one or more chemical compounds within the fluid (e.g., the concentration of one or more active agents added from reservoir 104 and/or the concentration of one or more materials being flushed from piping in fluid system 100), the temperature of the fluid, the conductivity of the fluid, the pH of the fluid, the flow rate at which the fluid moves through the optical sensor, and/or other characteristics of the fluid that may help ensure the system from which the fluid sample being analyzed is operating properly. Optical sensor 102 communicates detected characteristic information to controller 106 via connection 118.

In response to receiving the detected characteristic, processor 112 of controller 106 may compare the determined characteristic information to one or more thresholds stored in memory 114 such as one or more concentration thresholds. Based on the comparison, controller 106 may adjust fluid system 100, e.g., so that the detected characteristic matches a target value for the characteristic. In some examples, controller 106 starts and/or stops pump 108 or increases and/or decreases the rate of pump 108 to adjust the concentration of a chemical compound flowing through fluid pathway 110. Starting pump 108 or increasing the operating rate of pump 108 can increase the concentration of the chemical compound in the fluid. Stopping pump 108 or decreasing the operating rate of pump 108 can decrease the concentration of chemical compound in the fluid. In some additional examples, controller 106 may control the flow of water that mixes with a chemical compound in reservoir 104 based on determined characteristic information, for example, by starting or stopping a pump that controls the flow of water or by increasing or decreasing the rate at which the pump operates. Although not illustrated in the example fluid system 100 of FIG. 1, controller 106 may also be communicatively coupled to a heat exchanger, heater, and/or cooler to adjust the temperature of fluid flowing through fluid pathway 110 based on characteristic information received from optical sensor 102.

Optical sensor 102 may be implemented in a number of different ways in fluid system 100. In the example shown in FIG. 1, optical sensor 102 is positioned in-line with fluid pathway 110 to determine a characteristic of the fluid flowing through the fluid pathway. In other examples, a pipe, tube, or other conduit may be connected between fluid pathway 110 and a flow chamber of optical sensor 102. In such examples, the conduit can fluidly connect the flow chamber (e.g., an inlet of the flow chamber) of optical sensor 102 to fluid pathway 110. As fluid moves through fluid pathway 110, a portion of the fluid may enter the conduit and pass adjacent a sensor head positioned within a fluid chamber, thereby allowing optical sensor 102 to determine one or more characteristics of fluid flowing through the fluid pathway. When implemented to receive fluid directly from fluid pathway 110, optical sensor 102 may be characterized as an online optical sensor. After passing through the flow chamber, analyzed fluid may or may not be returned to fluid pathway 110, e.g., via another conduit connecting an outlet of the flow chamber to the fluid pathway.

In yet other examples, optical sensor 102 may be used to determine one or more characteristics of a stationary volume of fluid that does not flow through a flow chamber of the optical sensor. For example, optical sensor 102 may be implemented as an offline monitoring tool (e.g., as a handheld sensor), that requires filling the optical sensor with a fluid sample manually extracted from fluid system 100.

Fluid system 100 in the example of FIG. 1 also includes reservoir 104, pump 108, and fluid pathway 110. Reservoir 104 may be any type of container that stores a chemical agent for subsequent delivery including, e.g., a tank, a tote, a bottle, and a box. Reservoir 104 may store a liquid, a solid (e.g., powder), and/or a gas. Pump 108 may be any form of pumping mechanism that supplies fluid from reservoir 104. For example, pump 108 may comprise a peristaltic pump or other form of continuous pump, a positive-displacement pump, or any other type of pump appropriate for the particular application. In examples in which reservoir 104 stores a solid and/or a gas, pump 108 may be replaced with a different type of metering device configured to deliver the gas and/or solid chemical agent to an intended discharge location. Fluid pathway 110 in fluid system 100 may be any type of flexible or inflexible tubing, piping, or conduit.

Figure 2:
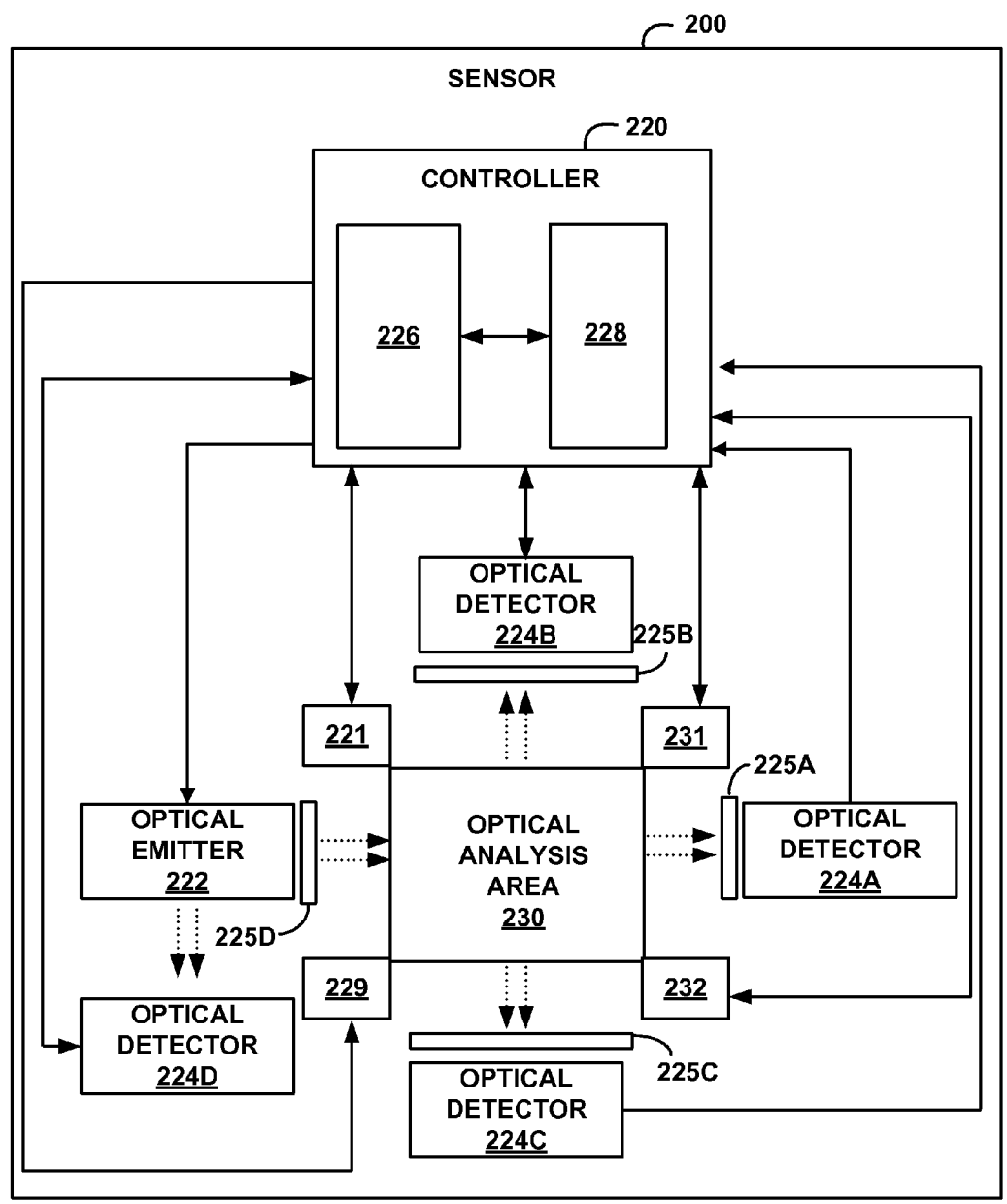
FIG. 2 is a block diagram illustrating an example optical sensor that may be used in the example fluid system of FIG. 1.

In the example of FIG. 1, optical sensor 102 determines a characteristic of the fluid flowing through fluid pathway 110 (e.g., concentration of a chemical compound, temperature or the like) and controller 106 controls fluid system 100 based on the determined characteristic and, e.g., a target characteristic stored in memory 114. FIG. 2 is block diagram illustrating an example of an optical sensor 200 that determines a characteristic of a fluid medium. Sensor 200 may be used as optical sensor 102 in fluid system 100, or sensor 200 may be used in other applications beyond fluid system 100.

With reference to FIG. 2, sensor 200 includes a controller 220, one or more optical emitters 222 (referred to herein as "optical emitter 222"), and one or more optical detectors which, in the illustrated example, is shown as including three optical detectors: first optical detector 224A, second optical detector 224B, and third optical detector 224C (collectively referred to therein as "optical detectors 224"). Sensor 200 also includes optical filters 225A-225D (collectively "optical filters 225") positioned between optical emitter 222/optical detectors 224 and optical analysis area 230. Controller 220 includes a processor 226 and a memory 228. In operation, optical emitter 222 directs light into a fluid sample filling optical analysis area 230. The fluid sample may be stationary within optical analysis area 230. Alternatively, the fluid sample may be flowing through optical analysis area 230. Regardless, in response to the light emitted by optical emitter 222, one or more of the optical detectors 224 may detect light emanating from or passing through the fluid. The characteristics of the fluid in optical analysis area 230 (e.g., the concentration of different chemical species in the fluid) may dictate whether light emitted by optical emitter 222 reaches any or all of optical detectors 224. Further, the position and configuration of each of optical detectors 224 relative to optical emitter 222 may influence whether the optical detectors detect light emitted by optical emitter 222 during operation.

In some examples, optical sensor 200 includes additional emitters and/or detectors. For example, optical sensor 200 may include a fourth detector 224D that functions as a reference detector. In operation, fourth detector 224D may receive unfiltered light from optical emitter 222 to monitor the output intensity of the optical emitter. Controller 220 may adjust measurements made by optical detectors 224A-224C to compensate for changes in the output of optical emitter 222, as determined based on data from fourth optical detector 224D.

Although sensor 200 is generally described as being an optical sensor, the sensor may include one or more non-optical sensor components for measuring additional properties of a fluid flowing through the sensor. In the example of FIG. 2, sensor 200 includes a temperature sensor 221, a pH sensor 229, a conductivity sensor 231, and a flow sensor 232. Temperature sensor 221 may sense a temperature of the fluid flowing through the sensor; pH sensor 229 may determine a pH of the fluid flowing through the sensor; and conductivity sensor 231 may determine an electrical conductivity of the fluid flowing through the sensor. Flow sensor 232 may monitor the flow rate at which fluid is flowing through the sensor.

In the configuration of sensor 200, first optical detector 224A, second optical detector 224B, and third optical detector 224C are each positioned on a different side of optical analysis area 230 than optical emitter 222. In particular, first optical detector 224A is positioned on an opposite side of optical analysis area 230 than optical emitter 222 (e.g., directly across the optical analysis area from the optical emitter). Second optical detector 224B is positioned at an approximately 90 degree angle relative to optical emitter 222. Further, third optical detector 224C is positioned on an opposite side of optical analysis area 230 from second optical detector 224B and also at an approximately 90 degree angle relative to optical emitter 222.

First optical detector 224A and second optical detector 224B in the example of FIG. 2 are configured to detect light directed by optical emitter 222 into fluid in optical analysis area 230 and passing through the fluid (e.g., either by direct transmission or by scattering/reflection). First optical detector 224A can detect light transmitted from optical emitter 222 across optical analysis area 230, such as light transmitted directly across the optical analysis area in a substantially linear transmission path. Second optical detector 224B can detect light transmitted from optical emitter 222 and scattered/reflected by fluid within optical analysis area 230. For example, second optical detector 224B can detect light transmitted from optical emitter 222 and scattered in an orthogonal (e.g., approximately 90 degree angle) relative to the direction of light emission. Third optical detector 224C in the example of FIG. 2 is configured to detect fluorescent emissions generated by the fluid in optical analysis area 230 in response to light from optical emitter 222.

In operation, first optical detector 224A and/or second optical detector 224B may be used to determine a concentration of a non-fluorescing species in the fluid sample under analysis whereas third optical detector 224C may be used to determine a concentration of a fluorescing species in the fluid sample under analysis. The amount of light detected by each of optical detectors 224 can be associated with different chemical concentration levels stored in memory 228. Accordingly, during use, processor 226 can receive signals from each of optical detectors 224 representative of the amount of light detected by each optical detector, compare and/or process the signals based on calibration information stored in memory 228, and determine the concentration of one or more chemical species in the fluid sample under analysis. By providing a first optical detector 224A and second optical detector 224B on different sides of optical analysis area 230, sensor 200 may determine a concentration for a non-fluorescing species over a wider range of concentrations than if the sensor includes only one of first optical detector 224A and second optical detector 224B.

As one example, sensor 200 may be used to monitor flushing water that is used to flush a piping system containing an optically opaque material such as milk. Sensor 200 may receive and evaluate samples of the flushing water throughout the flushing process. At the beginning of the flushing process, sensor 200 may receive a fluid sample that contains a high concentration of the optically opaque material. When optical emitter 222 directs light into this fluid sample, neither first optical detector 224A nor second optical detector 224B may detect any light, indicating that there is a high concentration of the optically opaque material in the sample. As the optically opaque material begins to clear from the piping system, sensor 200 may receive a fluid sample that contains a reduced amount of optically opaque material. When optical emitter 222 directs light into this fluid sample, first optical detector 224A may detect some light transmitting through the fluid sample and second optical detector 224B may or may not detect light scattering within the fluid sample. Sensor 200 can determine a concentration of the optically opaque material, e.g., based on a magnitude of the signal received from first optical detector 224A and calibration data stored in memory.

As the flushing process continues in this example, the optically opaque material may further clear from the piping system, e.g., until the piping system is substantially or entirely clear of the optically opaque material. Accordingly, sensor 200 may receive an additional fluid sample that contains a further reduced amount of optically opaque material. When optical emitter 222 directs light into this fluid sample, the amount of light passing through the fluid sample may saturate first optical detector 224A because the optical transparency of the fluid sample is so great. However, second optical detector 224B may detect light scattering within the fluid sample. The amount of light scattering may be dependent, e.g., on the concentration of the optically opaque material in the fluid sample and/or the turbidity of the fluid sample. Sensor 200 can determine a concentration of the optically opaque material, e.g., based on a magnitude of the signal received from second optical detector 224B and calibration data stored in memory.

In instances in which the flushing liquid also includes a fluorescing molecule, for example associated with a sanitizing agent, third optical detector 224C may detect fluorescent emissions emanating from the fluid sample in response to light emitted by optical emitter 222. Sensor 200 may then determine a concentration of the fluorescing material, e.g., based on a magnitude of the signal received from third optical detector 224A and calibration data stored in memory. In this way, sensor 200 can provide multiple detection channels associated with multiple optical detectors. The different optical detectors may be configured and arranged relative to optical emitter 222 to detect light traveling in different directions and/or different wavelengths of light. It should be appreciated that the foregoing discussion of a flushing process is merely one example implementation of sensor 200, and the disclosure is not limited in this respect.

To control the wavelengths of light emitted by optical emitter 222 and detected by optical detectors 224, sensor 200 may include optical filters 225. Optical filters 225 can filter wavelengths of light emitted by optical emitter 222 and/or received by optical detectors 224, e.g., so that only certain wavelengths of light are emitted into optical analysis area 230 and/or received from the optical analysis area. In the example of FIG. 2, a first optical detection filter 225A is positioned between first optical detector 224A and optical analysis area 230; a second optical detection filter 225B is positioned between second optical detector 224B and the optical analysis area; a third optical detection filter 225C is positioned between third optical detector 224C and the optical analysis area; and an optical emission filter 225D is positioned between optical emitter 222 and the optical analysis area. In operation, light emitted by optical emitter 222 passes through optical emission filter 225D. Optical emission filter 225D can filter out or remove certain wavelengths of light emitted by the optical emitter so that only select wavelengths of light pass through the filter. Likewise, optical detection filters 225A-225C can filter out or remove certain wavelengths of light so that only select wavelengths of light are received by optical detectors 224. When used, reference optical detector 224D can be positioned in a variety of locations within sensor 200. In different examples, reference optical detector 224D can be positioned to receive a portion of the light emitted by optical emitter 222 but not filtered, a portion of the light reflected by filter 225D, and/or a portion of the light transmitted through filter 225D from optical emitter 222.

The wavelengths of light that optical filters 225 are designed to filter out may vary, e.g., depending on the expected chemical composition of the fluid in optical analysis area 230 and the design parameters of optical emitter 222 and optical detectors 224. In applications where first optical detector 224A and second optical detector 224B are configured to detect light passing through a fluid sample, first optical detection filter 225A and second optical detection filter 225B may be configured to pass the same wavelengths of light passing through optical emission filter 225D while rejecting all other wavelengths of light. By contrast, third optical detection filter 225C may be configured to reject (e.g., filter out) those wavelengths of light emitted by optical emitter 222 and pass different wavelengths of light corresponding to the portion of the spectrum in which a fluorescing molecule in the fluid sample emits. Third optical detection filter 225C may filter out different wavelengths of light than optical emission filter 225D because when optical emitter 222 directs light at one frequency (e.g., ultraviolet frequency) into fluid flowing through optical analysis area 230, fluorescing molecules may emit light energy at a different frequency (e.g., visible light frequency, a different ultraviolet frequency).

In practice, first optical filter 225A, second optical filter 225B, and optical emission filter 225D may each be the same type of filter that filters out the same wavelengths of light. By contrast, third optical filter 225C may be configured to reject (e.g., filter out) all wavelengths of light that can pass through first optical filter 225A, second optical filter 225B, and optical emission filter 225D and allow passage of wavelengths of light in a portion of the spectrum a fluorescing molecule in the fluid sample is expected to emit. For example, first optical filter 225A, second optical filter 225B, and optical emission filter 225D may each be configured to filter out wavelengths of light greater than 300 nanometers so that only wavelengths of light less than 300 nanometers can pass through the filters. In accordance with this example, third optical detector filter 225C may filter out wavelengths of light less than 300 nanometers so that only wavelengths of light greater than 300 nanometers can pass through the filter.

By configuring first optical filter 225A and second optical filter 225B to be the same optical filter as optical emission filter 225D, substantially any light (e.g., all light) detected by first optical detector 224A and second optical detector 224B during operation will be light emitted by optical emitter 222 that passes through optical emission filter 225D and the fluid sample. Further, by configuring third optical filter 225C to reject wavelengths of light passing through optical emission filter 225D, substantially any light (e.g., all light) detected by third optical detector 224C will be light emitted by fluorescing molecules in the fluid sample. In contrast, if first optical filter 225A and second optical filter 225B were to pass different wavelengths of light than optical emission filter 225D, first optical detector 224A and second optical detector 224B may detect light from sources other than optical emitter 222, such as light emitted by fluorescing molecules. Likewise, if third optical filter 225C were to pass wavelengths of light emitted by optical emitter 222, third optical detector 224C may detect light from sources other than fluorescing molecules, such as light emitted by the optical emitter itself.

In some examples, all three filters 225A, 225B, 225C are configured to reject wavelengths of light passing through optical emission filter 225D so that substantially any light (e.g., all light) detected by all three optical detectors 224A, 224B, 224C will be light emitted by fluorescing molecules in the fluid sample. Such a configuration may be used to detect multiple (e.g., three) different spectral areas of fluorescence to measure multiple spectral components simultaneously. For instance, signals from one or two detectors measuring different spectral areas may be used to compensate for interference from compounds present in a fluid and producing fluorescence masking a desired signal from the third detector. As an example, fluorescence from natural substances such as milk may be present in a fluid and can interfere with fluorescence emitted from a chemical compound in the fluid (e.g., a cleaning agent, sanitizing agent, tracer) whose concentration is being measured by sensor 200. To help compensate for this fluorescence masking, different spectral areas (e.g., different wavelengths) of the fluorescent emissions from the fluid can be detected and used to computationally compensate for the interference.

While sensor 200 in the example of FIG. 2 includes optical filters 225, in other examples, sensor 200 may not include optical filters 225 or may have a different number or arrangement of optical filters. For example, the physical filter positioned between optical emitter 222 and optical analysis area 230 may not be needed if a laser light source is used providing a highly monochromatic excitation beam. Additionally, some or all of optical filters 225A-225C for the detectors may not be needed if the spectral sensitivity of the detector(s) provides adequate rejection of excitation light and/or fluorescence light. As another example, if sensor 200 is configured to measure time delayed fluorescence or scattering, time filtration can be used instead of physical spectral filtration. In such cases, the optical filters 225 may be programs stored in memory 228 that are executed by processor 226 to electronically filter data generated by sensor 200.

Sensor 200 in FIG. 2 includes optical emitter 222. Optical emitter 222 can emit optical energy into a fluid present with optical analysis area 230. In some examples, optical emitter 222 emits optical energy over a range of wavelengths. In other examples, optical emitter 222 emits optical energy at one or more discrete wavelengths. For example, optical emitter 222 may emit at two, three, four or more discrete wavelengths. Further, although sensor 200 is only illustrated as having only a single optical emitter, in other applications, sensor 200 may have a plurality (e.g., two, three, four, or more) of optical emitters.

In one example, optical emitter 222 emits light within the ultraviolet (UV) spectrum and/or in the visible range of the spectrum. Light within the UV spectrum may include wavelengths in the range from approximately 200 nm to approximately 400 nanometers. Light within the visible spectrum may include wavelengths in the range from approximately 400 nm to approximately 700 nm. Light emitted by optical emitter 222 is directed into fluid within optical analysis area 230. In response to receiving the optical energy, fluorescing molecules within the fluid may excite, causing the molecules to produce fluorescent emissions. For example, the light directed into the fluid by optical emitter 222 may generate fluorescent emissions by exciting electrons of fluorescing molecules within the fluid, causing the molecules to emit energy (i.e., fluoresce). The fluorescent emissions, which may or may not be at a different frequency than the energy emitted by optical emitter 222, may be generated as excited electrons within fluorescing molecules change energy states. The energy emitted by the fluorescing molecules may be detected by third optical detector 224C.

Optical emitter 222 may be implemented in a variety of different ways within sensor 200. Optical emitter 222 may include one or more light sources to excite molecules within the fluid. Example light sources include light emitting diodes (LEDS), lasers, and lamps. In some examples, as discussed above, optical emitter 222 includes an optical filter to filter light emitted by the light source. The optical filter may be positioned between the light source and the fluid and be selected to pass light within a certain wavelength range. In some additional examples, the optical emitter includes a collimator, e.g., a collimating lens, hood or reflector, positioned adjacent the light source to collimate the light emitted from the light source. The collimator may reduce the divergence of the light emitted from the light source, reducing optical noise.

Sensor 200 also includes optical detectors 224. Optical detectors 224 may include at least one optical detector that detects fluorescent emissions emitted by excited molecules within optical analysis area 230 (e.g., third optical detector 224C) and at least one optical detector that detects light emitted by optical emitter 222 and passing through fluid in the optical analysis area (e.g., first optical detector 224A and/or second optical detector 224B). In operation, the amount of optical energy detected by each optical detector of optical detectors 224 may depend on the contents of the fluid within optical analysis area 230. If the optical analysis area contains a fluid solution that has certain properties (e.g., a certain chemical compound and/or a certain concentration of a chemical species), each optical detector of optical detectors 224 may detect a certain level of fluorescent energy emitted by the fluid and/or transmitted through or scattered by the fluid. However, if the fluid solution has different properties (e.g., a different chemical compound and/or a different concentration of the chemical species), each optical detector of optical detectors 224 may detect a different level of fluorescent energy emitted by the fluid and/or a different level of optical energy transmitted through or scattered by the fluid. For example, if a fluid within optical analysis area 230 has a first concentration of a fluorescing chemical compound(s), third optical detector 224C may detect a first magnitude of fluorescent emissions. However, if the fluid within optical analysis area 230 has a second concentration of the fluorescing chemical compound(s) that is greater than the first concentration, third optical detector 224C may detect a second magnitude of fluorescent emissions that is greater than the first magnitude.

Each optical detector of optical detectors 224 may be implemented in a variety of different ways within sensor 200. Each optical detector of optical detectors 224 may include one or more photodetectors such as, e.g., photodiodes or photomultipliers, for converting optical signals into electrical signals. In some examples, each optical detector of optical detectors 224 includes a lens positioned between the fluid and the photodetector for focusing and/or shaping optical energy received from the fluid. In addition, while sensor 200 in the example of FIG. 2 includes three optical detectors 224A-224C, in other examples, sensor 200 may include fewer optical detectors (e.g., a single optical detector such as 224B or 224C) or more optical detectors (e.g., four, five, or more). It should be appreciated that the disclosure is not limited to a sensor having any specific number of optical detectors.

Sensor 200 in the example of FIG. 2 also includes temperature sensor 221. Temperature sensor 221 is configured to sense a temperature of a fluid passing through a flow chamber of the sensor. In various examples, temperature sensor 221 may be a bi-metal mechanical temperature sensor, an electrical resistance temperature sensor, an optical temperature sensor, or any other suitable type of temperature sensor. Temperature sensor 221 can generate a signal that is representative of the magnitude of the sensed temperature.

Controller 220 controls the operation of optical emitter 222 and receives signals concerning the amount of light detected by each optical detector of optical detectors 224. Controller 220 also received signals from temperature sensor 221 concerning the temperature of the fluid in contact with the sensor, signals from pH sensor 229 concerning the pH of the fluid in contact with the sensor, signals from conductivity sensor 231 concerning the conductivity of the fluid in contact with the sensor, and signals from flow sensor 232 concerning the rate at which liquid is flowing through the sensor. In some examples, controller 220 further processes signals, e.g., to determine a concentration of one or more chemical species within the fluid passing through fluid channel 230.

In one example, controller 220 controls optical emitter 222 to direct radiation into a fluid and further controls each optical detector of optical detectors 224 to detect fluorescent emissions emitted by the fluid and/or light transmitted through or scattered by the fluid. Controller 220 then processes the light detection information. For example, controller 220 can process the light detection information received from third optical detector 224C to determine a concentration of a chemical species in the fluid. In instances in which a fluid includes a fluorescent tracer, a concentration of a chemical species of interest can be determined based on a determined concentration of the fluorescent tracer. Controller 220 can determine a concentration of the fluorescent tracer by comparing the magnitude of fluorescent emissions detected by third optical detector 224C from a fluid having an unknown concentration of the tracer to the magnitude of the fluorescent emissions detected by third optical detector 224C from a fluid having a known concentration of the tracer. Controller 220 can determine the concentration of a chemical species of interest using Equations (1) and (2) below:

$$C_c = C_m \times \frac{C_o}{C_f} \qquad \text{Equation 1}$$

$$C_m = K_m \times (S_x - Z_o) \qquad \text{Equation 2}$$

In Equations (1) and (2) above, $C_c$ is a current concentration of the chemical species of interest, $C_m$ is a current concentration of the fluorescent tracer, $C_o$ is a nominal concentration of the chemical species of interest, $C_f$ is a nominal concentration of the fluorescent tracer, $K_m$ is a slope correction coefficient, $S_x$ is a current fluorescent measurement signal, and $Z_o$ is a zero shift. Controller 220 may further adjust the determined concentration of the chemical species of interest based on the temperature measured by temperature sensor 221.

Controller 220 may also process light detection information received from first optical detector 224A and/or second optical detector 224B to determine other aspects of the fluid under analysis, such as a concentration of a non-fluorescing chemical species in the fluid. Controller 220 can determine a concentration of the non-fluorescing chemical species by comparing the magnitude of light detected by first optical detector 224A and/or second optical detector 224B from a fluid having an unknown concentration of the species to the magnitude of light detected by first optical detector 224A and/or second optical detector 224B from a fluid having a known concentration of the species. Controller 220 may compare the determined concentration to one or more thresholds stored in memory 228. For example, when controller 220 is used to monitor flushing water, the controller may compare the determined concentration of the non-fluorescing species to one or more thresholds stored in memory. Controller 220 may further adjust the flushing process (e.g., to start, stop, or adjust flushing water rates) based on the comparison.

Optical analysis area 230 in sensor 200 may be a region of the sensor where fluid can reside and/or pass through for optical analysis. In one example, optical analysis area 230 comprises a tube of optically transparent material (e.g., glass, plastic, sapphire) through which light can be emitted and received. The tube may define an internal diameter and an external diameter, where a wall thickness of the tube separates the internal diameter from the external diameter. In another example, optical analysis area 230 is a region of a flow chamber housing through which liquid flows for optical analysis. Although optical analysis area 230 is conceptually illustrated as being square in cross-sectional shape, the area can define any polygonal (e.g., triangle, hexagon) or arcuate (e.g., circular, elliptical) shape or even combinations of polygonal and arcuate shapes. In addition, while optical analysis area 230 can be of any size, in some applications, the optical analysis area is comparatively small to minimize the amount of fluid that is needed to fill the optical analysis area. For example, optical analysis area 230 may define a major cross-sectional dimension (e.g., diameter) less than 15 millimeters (mm), such as less than 10 mm, or less than 5 mm. In one example, optical analysis area 230 is a tube having an outer diameter ranging from approximately 10 mm to approximately 4 mm, a wall thickness ranging from approximately 3 mm to approximately 1 mm, and an internal diameter ranging from approximately 9 mm to approximately 1 mm.

Memory 228 of sensor 200 stores software and data used or generated by controller 220. For example, memory 228 may store data used by controller 220 to determine a concentration of one or more chemical components within the fluid being monitored by sensor 200. In some examples, memory 228 stores data in the form of an equation that relates light detected by optical detectors 224 to a concentration of one or more chemical components.

Processor 226 runs software stored in memory 228 to perform functions attributed to sensor 200 and controller 220 in this disclosure. Components described as processors within controller 220, controller 106, or any other device described in this disclosure may each include one or more processors, such as one or more microprocessors, digital signal processors (DSPs), application specific integrated circuits (ASICs), field programmable gate arrays (FPGAs), programmable logic circuitry, or the like, either alone or in any suitable combination.

Figure 3:
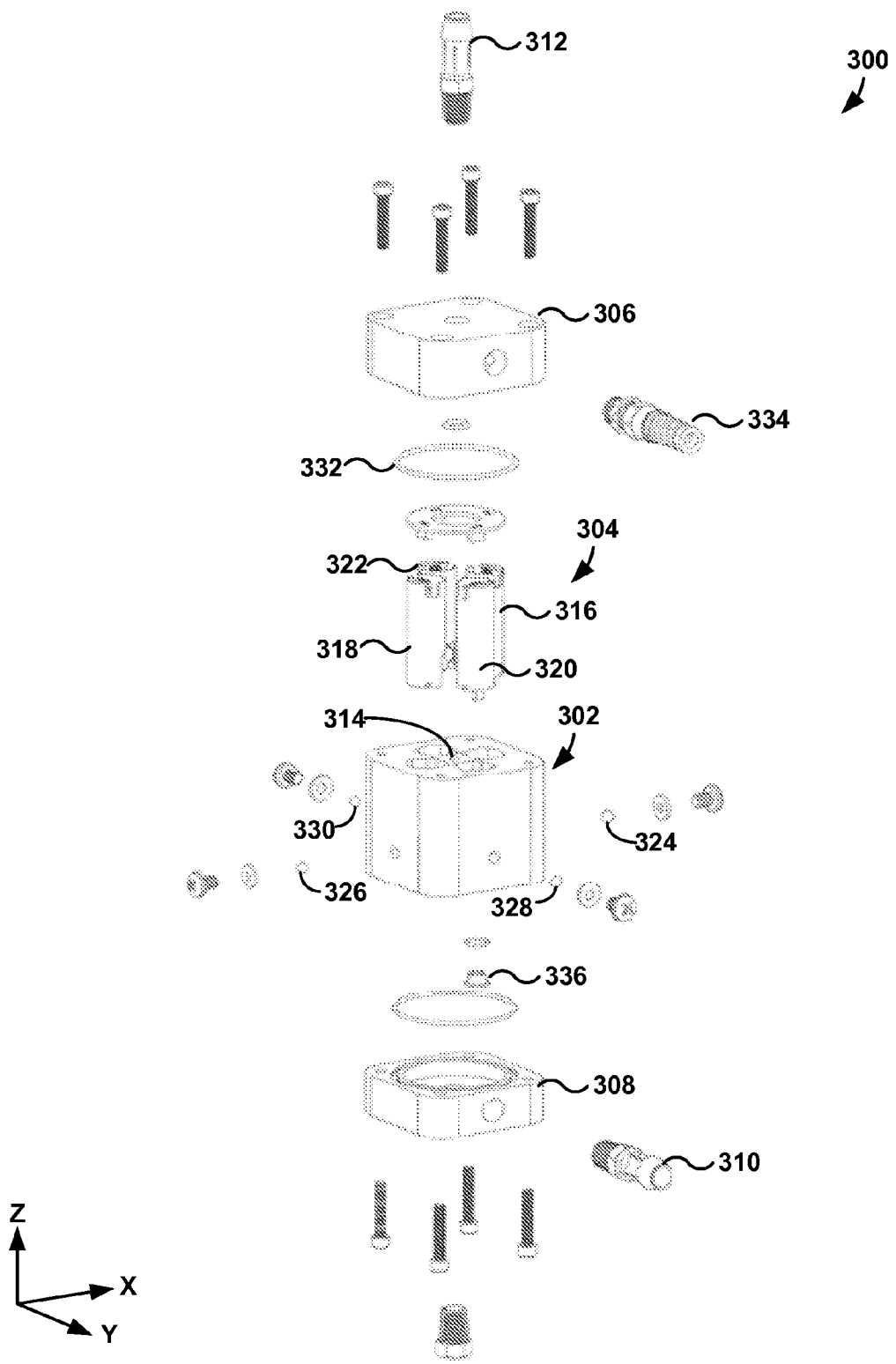
FIG. 3 is a schematic drawing of an example physical configuration of an optical sensor that may be used by the optical sensors in FIGS. 1 and 2.

Sensor 102 (FIG. 1) and sensor 200 (FIG. 2) can have a number of different physical configurations. FIG. 3 is a schematic drawing of one example configuration of a sensor 300, which can be used by sensor 102 and sensor 200. Sensor 300 includes a flow chamber 302, a light emission/detection assembly 304, a flow chamber top cover 306, and a flow chamber bottom cover 308. Flow chamber 302 has an inlet 310 that receives fluid (e.g., from fluid pathway 110 in FIG. 1), an outlet 312 that discharges the fluid after optical analysis inside of the flow chamber, and an optical analysis area 314 between the inlet and outlet.

Light emission/detection assembly 304 is shown outside of and insertable into flow chamber 302. Light emission/detection assembly 304 includes an optical emitter assembly 316 that carries an optical emitter, a first optical detector assembly 318 that carries a first optical detector, a second optical detector assembly 320 that carries a second optical detector, and a third optical detector assembly 322 that carries a third optical detector. In operation, the optical emitter carried by optical emitter assembly 316 can emit optical energy through a first optical window 324 into optical analysis area 314. This first optical window 324 may be referred to as an optical emitter window. The first optical detector carried by the first optical detector assembly 318 can detect light emitted by the optical emitter and transmitted across optical analysis area 314 and received through a second optical window 326. This second optical window 326 may be referred to as a first optical detector window. The second optical detector carried by the second optical detector assembly 320 can detect light emitted by the optical emitter and scattered in a direction substantially orthogonal to the direction of emission through a third optical window 328. This third optical window 328 may be referred to as a second optical detector window. In addition, the third optical detector carried by the third optical detector assembly 322 can detect fluorescent emissions from within optical analysis area 314 through a fourth optical window 330. This fourth optical window 330 may be referred to as a third optical detector window.

Optical windows 324, 326, 328, and 330 are shown as being positioned outside of flow chamber 302 and insertable into the flow chamber. When inserted into the flow chamber, the optical windows may define fluid tight, optically transparent regions through which light can be emitted into optical analysis area 314 and detected from the optical analysis area. Optical windows 324, 326, 328, and 330 may or may not include a lens, prism, or other optical device that transmits and refracts light. In the illustrated example, optical windows 324, 326, 328, and 330 are formed by a ball lens positioned within an insertion channel extending through flow chamber 302. The ball lenses can be fabricated from glass, sapphire, or other suitable optically transparent materials. In different examples, optical windows 324, 326, 328, and 330 may not be removable but may instead be permanently formed/mated with flow chamber 302.

In addition to flow chamber 302 and light emission/detection assembly 304, sensor 300 in the example of FIG. 3 also includes an electrical connection board 332, an electrical cable 334, and a temperature sensor 336. Electrical connection board 332 electrically couples optical emitter assembly 316, first optical detector assembly 318, second optical detector assembly 320, and third optical detector assembly 322 to electrical cable 334. Electrical cable 334 may convey electrical signals transmitted to or generated by sensor 300. Electrical cable 334 may or may not also convey power to sensor 300 to power the various components of the sensor. Temperature sensor 336 can sense a temperature of the fluid entering optical analysis area and generate a signal corresponding to the sensed temperature.

Figure 4:
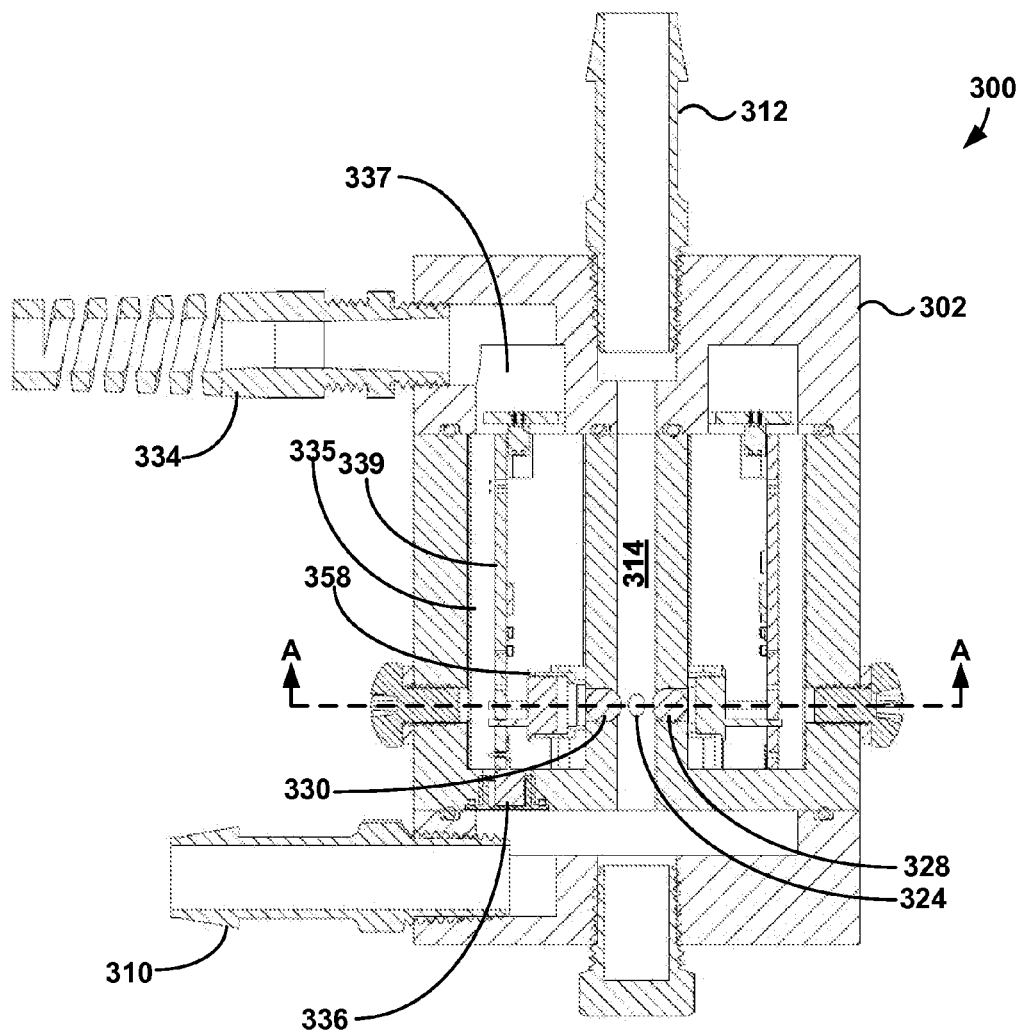
FIGS. 4 and 5 are cross-sectional drawings of the optical sensor of FIG. 3.

FIG. 4 is a cross-sectional illustration of sensor 300 taken in a Z-Y plane indicated on FIG. 3 that bisects third optical window 328 and fourth optical window 330. Like components of sensor 300 in FIGS. 3 and 4 are identified by like reference numbers. As shown in FIG. 4, optical windows 324, 328, and 330 are each positioned within flow chamber 302 to direct light into or to receive light from optical analysis area 314. Optical analysis area 314 is a flow path defined in flow chamber 302 through which fluid can travel past the optical windows of the sensor for optical analysis. In the illustrated example, optical windows 324, 328, and 330 are positioned at a co-planar location (i.e., co-planar in the X-Y plane indicated on FIG. 4) along optical analysis area 314, e.g., so that a common plane extends through a geometric center of optical windows 324, 328, and 330. Second optical window 326 (not illustrated on FIG. 4) may be positioned in the same plane as optical windows 324, 328, and 330. Positioning optical windows 324, 326, 328, and 330 in a common plane may be useful so that the optical detectors positioned behind optical windows 326, 328, and 330 receive light from the same plane in which the optical emitter positioned behind optical window 324 emits into. If optical windows 326, 328, and 330 are offset from the plane in which optical window 324 is positioned, the amount of light detected by, and hence the strength of signal generated by, the detectors positioned behind the windows may be reduced as compared to a co-planar location.

While optical sensor 300 is illustrated as only having a single row of optical windows 324, 326, 328, and 330 positioned in a common plane for optical emitter 222 and optical detectors 224, in examples in which the optical sensor has more optical emitters and/or detectors, the sensor can have one or more additional rows of optical windows. For example, optical sensor 300 may include two, three, or more vertically stacked (i.e., in the Z-direction indicated on FIG. 4) rows of optical windows, where optical windows in each row are co-planar (i.e., co-planar in the X-Y plane indicated on FIG. 4). In one example, optical sensor 300 includes three rows of optical windows, where each row includes one optical emitter and three optical detectors. As another example, optical sensor 300 includes two rows of optical windows, where each row includes two optical emitters and two optical detectors. Increasing the number of optical emitters and/or optical detectors in sensor 300 can increase the number of wavelengths of light emitted in and/or detected from fluid flowing through fluid pathway 314.

FIG. 4 also illustrates temperature sensor 336. Temperature sensor 336 is positioned within a common well 335 of optical housing 302 that contains optical detector 358. Temperature sensor 336 extends through a bottom of the well so that the sensor contacts fluid flowing through the optical sensor to sense a temperature of the fluid. In the example, the temperature sensor 336 is formed on a circuit board 339, which is the same circuit board containing optical detector 358. That is, a single circuit board contains the same electronics for the temperature sensor as the optical detector. Such a configuration may be useful to make a more compact optical sensor.

In some examples, sensor 300 includes additional non-optical sensor components, such as a pH sensor, a conductivity sensor, and a flow sensor. When used, each of the non-optical sensors may be formed on a common circuit board with one of the optical emitters (e.g., the electronics for one of the optical emitters) and/or optical detectors (e.g., electronics for the optical detectors) of the sensor positioned within a common well of the housing. For example, electronic components for the pH sensor may be formed on the same circuit board as one optical detector, electronic components for the conductivity sensor may be formed on the same circuit board as a different optical detector, and electronic components for temperature sensor 336 may be formed on circuit board 339 of yet another optical detector. Each sensor may extend through a bottom of a respective well of optical housing 102 (e.g., as shown for temperature sensor 336 in FIG. 4) to contact fluid flowing through the sensor. When used, the flow sensor may also be formed on the same circuit board as one of the optical emitters/optical detectors. As an example, electronics for a differential pressure flow sensor may be formed on the same circuit board as one of the optical emitters/optical detectors with the flow sensor positioned in region 337 to measure flow adjacent outlet 312.

Figure 5:
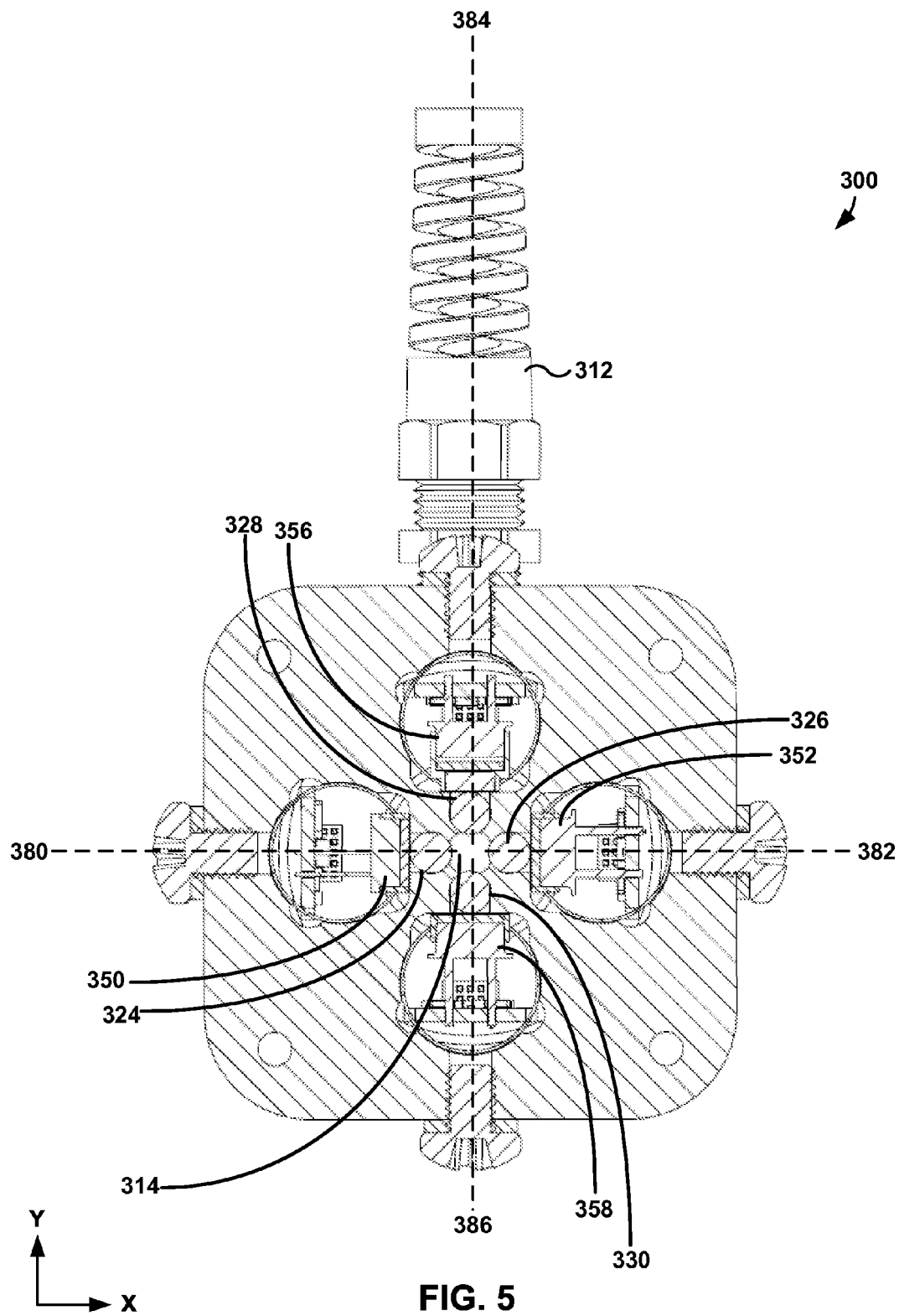

FIG. 5 is a cross-sectional illustration of sensor 300 taken along the A-A line indicated on FIG. 4. Again, like components of sensor 300 in FIGS. 3-5 are identified by like reference numbers. As shown in this example, an optical emitter 350 is positioned (e.g., centered) behind first optical window 324, and a first optical detector 352 is positioned (e.g., centered) behind second optical window 326. First optical detector 352 is positioned on an opposite side of optical analysis area 314, e.g., so that light emitted from optical emitter 350 traveling in a linear or substantially linear direction and transmitted through fluid in the optical analysis area is received by the first optical detector. In some examples, first optical detector 352 is positioned on an opposite side of optical analysis area 314 so that an axis 380 located in a common plane of optical windows 324, 326, 328, 330 (e.g., a common X-Y plane indicated on FIGS. 4 and 5) and extending through a geometric center of first optical window 324 intersects second optical window 326 across optical analysis area 314. For example, axis 380 extending through a geometric center of first optical window 324 may intersect an axis 382 that is located in the common plane of optical windows 324, 326, 328, 330 and that extends through a geometric center of second optical window 326. In such a configuration, second optical widow 326 may be positioned directly across the optical analysis area 314 from first optical window 324. In other examples, as described in greater detail below with respect to FIG. 6, second optical window 326 may be positioned across optical analysis area 314 from first optical window 324 but may be offset from the first optical window (e.g., in the positive or negative Y-direction indicated on FIG. 5).

In the example of FIG. 5, sensor 300 also includes a second optical detector 356 positioned (e.g., centered) behind the third optical window 328 and a third optical detector 358 positioned (e.g., centered) behind the fourth optical window 330. Second optical detector 356 is positioned at an approximately 90 degree angle with respect to optical emitter 350, e.g., so that light emitted from optical emitter 350 traveling in a linear or substantially linear direction must scatter in a generally orthogonal direction and be transmitted through fluid in the optical analysis area in order to be received by the second optical detector. Third optical detector 358 is positioned opposite second optical detector 356 across optical analysis area 314. Third optical detector 358 is also positioned at an approximately 90 degree angle with respect to optical emitter 350, e.g., so that light emitted from optical emitter 350 traveling in a linear or substantially linear direction must scatter in a generally orthogonal direction and be transmitted through fluid in the optical analysis area in order to be received by the third optical detector.

In some examples, second optical detector 356 is positioned at an approximately 90 degree angle with respect to optical emitter 350 so that an axis 384 in a common plane of optical windows 324, 326, 328, 330 (e.g., a common X-Y plane indicated on FIGS. 4 and 5) and extending through a geometric center of third optical window 328 intersects axis 380 at an approximately 90 degree angle (e.g., an angle ranging from 60 degrees to 120 degrees). Third optical detector 358 may be positioned at an approximately 90 degree angle with respect to optical emitter 350 so that an axis 386 in a common plane of optical windows 324, 326, 328, 330 (e.g., a common X-Y plane indicated on FIGS. 4 and 5) and extending through a geometric center of fourth optical window 330 intersects axis 380 at an approximately 90 degree angle (e.g., an angle ranging from 60 degrees to 120 degrees). In different examples, axis 384 and axis 386 may intersect one another so that the third optical window is positioned directly across from the fourth optical window, or axis 384 and axis 386 may be offset from one another (e.g., in the positive or negative X-direction indicated on FIG. 5) so that third optical window is offset from fourth optical window. Positioning third optical window 328 and fourth optical window 330 (and the corresponding detectors positioned behind the optical windows) at an angle relative to first optical window 324 (and the corresponding optical emitter positioned behind the window) may be useful to limit the amount of light received by the detectors. If the detectors receive too much light, the detectors may become saturated and cease providing useful analysis information.

When sensor 300 is arranged as illustrated in FIG. 5, optical emitter 350 and optical detectors 352, 356, 358 may each be centered about optical analysis area 314 so as to emit light towards and receive light from a geometric center of the optical analysis area. Such a configuration may be useful for providing a central area of optical inspection into which light is directed and received during operation of sensor 300. In other examples, however, one or more of optical emitter 350 and optical detectors 352, 356, 358 may be offset from optical analysis area 314 so that light is not emitted towards and/or received from a center of the optical analysis area but rather at an off-center region of the optical analysis area.

Applicant has found that, in some examples, moving an optical emitter so that the emitter directs light adjacent a wall of an optical analysis area rather than at a center of the optical analysis area can increase the amount of light detected by, and hence, strength of signal generated from, an optical detector positioned to receive light from the optical analysis area. For example, the strength of signal generated by an optical detector positioned to receive light from the optical analysis area may be from approximately 2 to approximately 5 times stronger when the optical emitter is offset to direct light adjacent a wall of an optical analysis area rather than at a center of the optical analysis area. Increased signal strength may be useful for a variety of reasons. As one example, in applications where fouling builds up on an optical detector during service, the ability to generate stronger signals can extend the length of time the optical sensor can remain in service between cleaning and maintenance.

Without wishing to be bound by any particular theory, it is believed that offsetting an optical emitter relative to a center of an optical analysis area may reduce the amount of light that is reflected in the optical analysis area (e.g., due to turbidity of the fluid sample and/or reflection off internal or external surfaces of the optical analysis area) as compared to if the optical emitter is positioned to direct light at the center of an optical analysis area. In turn, this can increase the strength of the signal generated by one or more optical detectors surrounding the optical analysis area.

Figure 6:
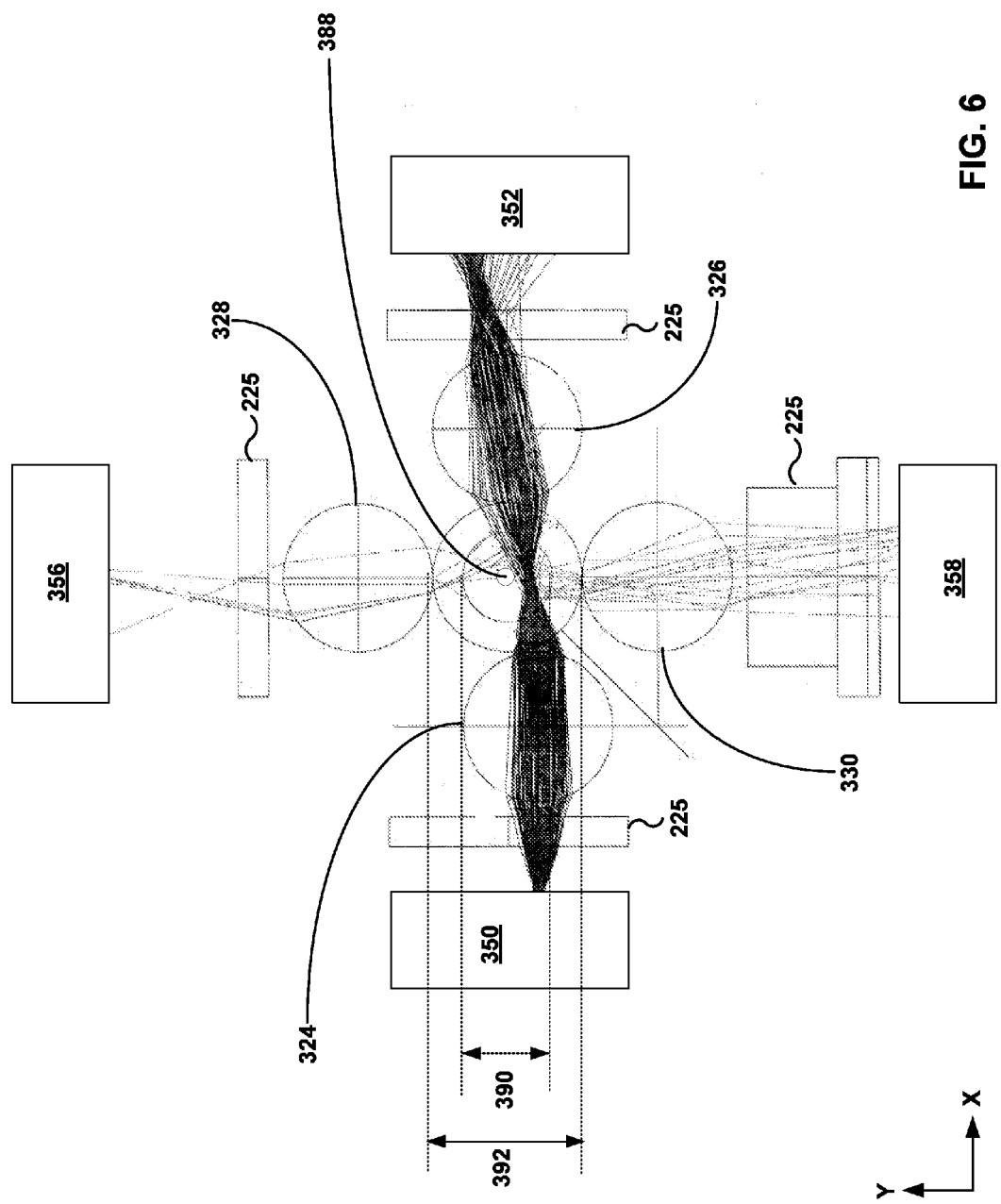
FIG. 6 is a cross-sectional drawing of an example alternative configuration of the optical sensor of FIG. 3.

FIG. 6 is a cross-sectional drawing showing an alternative configuration of sensor 300 in which the optical emitter has been offset relative to the center of the optical analysis area. Like components of sensor 300 in FIGS. 3-6 are identified by like reference numbers. For example, sensor 300 in FIG. 6 is illustrated as including optical emitter 350, first optical detector 352, second optical detector 356, and third optical detector 358. Optical emitter 350 is positioned behind first optical window 324; first optical detector 352 is positioned behind second optical window 326; second optical detector 356 is positioned behind third optical window 328; a third optical detector 358 positioned behind fourth optical window 330. Optical windows 324, 326, 328, 330 each face optical analysis area 314 to direct light into and receive light from a fluid sample present in the optical analysis area. In addition, sensor 300 in FIG. 6 includes optical filters 225 (FIG. 2) positioned between the optical emitter/detectors and optical windows 324, 326, 328, 330. In other examples, sensor 300 may not include the optical filters or may have a different number or arrangement of optical filters.

In contrast to the configuration of optical sensor 300 in FIG. 5, in the example configuration of FIG. 6, first optical window 324 (e.g., the optical emitter window) is offset relative to a center of optical analysis area 314. In particular, first optical window 324 is positioned closer to fourth optical window 330 (e.g., the third optical detector window) than third optical window 328 (e.g., the second optical detector window). In operation, light emitted by optical emitter 350 and traveling in a linear direction through a geometric center of first optical window 324 may not be directed at nor intersect a geometric center of optical analysis area 314. Rather, by offsetting optical emitter window 324, the light may be directed closer to a wall of optical analysis area 314 than if the light were directed at a geometric center of the optical analysis area.

For example, in FIG. 6, optical analysis area 314 defines a geometric center 388. The geometric center 388 may be an arithmetic mean location of all points around the perimeter bounding the optical analysis area. For instance, where optical analysis area 314 is a circular tube, the geometric center 388 may be a point in the interior of the circle that is equidistance from all points on the circumference of the circle. By offsetting first optical window 324 relative to geometric center 388, light emitted through the optical analysis window may not converge at the geometric center of the optical analysis area. Rather, the light may converge at a location between the geometric center 388 of optical analysis area 314 and a wall bounding the optical analysis area.

In the example of FIG. 6, optical analysis area 314 is illustrated as a fluid tube (e.g., glass tube, quartz tube, sapphire tube) that defines an internal diameter 390 and an external diameter 392, where the internal diameter is separated from the external diameter by a wall thickness of the tube. Optical windows 324, 326, 328, and 330 are positioned adjacent to and, in some examples, in contact with an external surface of the fluid tube. In addition, in FIG. 6, optical windows 324, 326, 328, and 330 are ball lenses that have a diameter larger than the internal diameter 390 of the fluid tube. Other configurations of optical windows 324, 326, 328, and 330 and optical analysis area 314 are possible for sensor 300.

Optical emitter 350 and/or first optical window 324 can be offset relative to a geometric center of optical analysis area 314 in a variety of different ways. In the example of FIG. 6, optical emitter 350 and first optical window 324 are moved in the negative Y-direction relative to second optical window 326 so that light traveling linearly from a geometric center of first optical window is directed closer to third optical detector 358 than second optical detector 356. In other examples, optical emitter 350 and first optical window 324 may be moved in the positive Y-direction relative to second optical window 326 so that light traveling linearly from a geometric center of first optical window 324 is directed closer to second optical detector 356 than third optical detector 358.

In some examples, optical emitter 350 and/or first optical window 324 is positioned so that an axis 380 (FIG. 5) located in a common plane of optical windows 324, 326, 328, 330 and extending through a geometric center of first optical window 324 does not intersect an axis 382 that is located in the common plane of optical windows 324, 326, 328, 330 and that extends through a geometric center of second optical window 326. While the distance first optical window 324 is offset relative to geometric center 388 may vary, e.g., based on the size of the optical window and the configuration of the sensor, in some examples, geometric center of the first optical window is offset (e.g., in the positive or negative Y-direction indicated on FIG. 6) from geometric center 388 a distance ranging from approximately 0.5 millimeters to approximately 10 millimeters, such as a distance ranging from approximately 1 millimeter to approximately 3 millimeters. Positioning first optical window 324 so that light emitted by optical emitter 350 is directed adjacent a wall of optical analysis area 314 may increase the strength of the signals generated by optical detectors 352, 356, 358.

The strength of signals detected by optical detectors 352, 356, 358 will vary, e.g., depending on the design of the specific detectors and the configuration of optical sensor 300. In one example in which optical sensor 300 is arranged as illustrated in FIG. 6 (and where optical analysis area 314 is a quartz tube having a 3 mm internal diameter and a 5 mm external diameter and first optical window 224 is offset in the negative Y-direction by 1 mm), it is expected that third optical detector 358 will provide a fluorescence signal of 19.9—micro-Watts (µW). By contrast, if optical windows 324, 326, 328, and 330 were symmetrical around optical analysis area 314 so that first optical window 224 was not offset in the negative Y-direction, it is expected that third optical detector 358 would provide a fluorescence signal of 10.5 µW under similar conditions (e.g., similar fluid flowing through optical analysis area 314).

Figure 7:
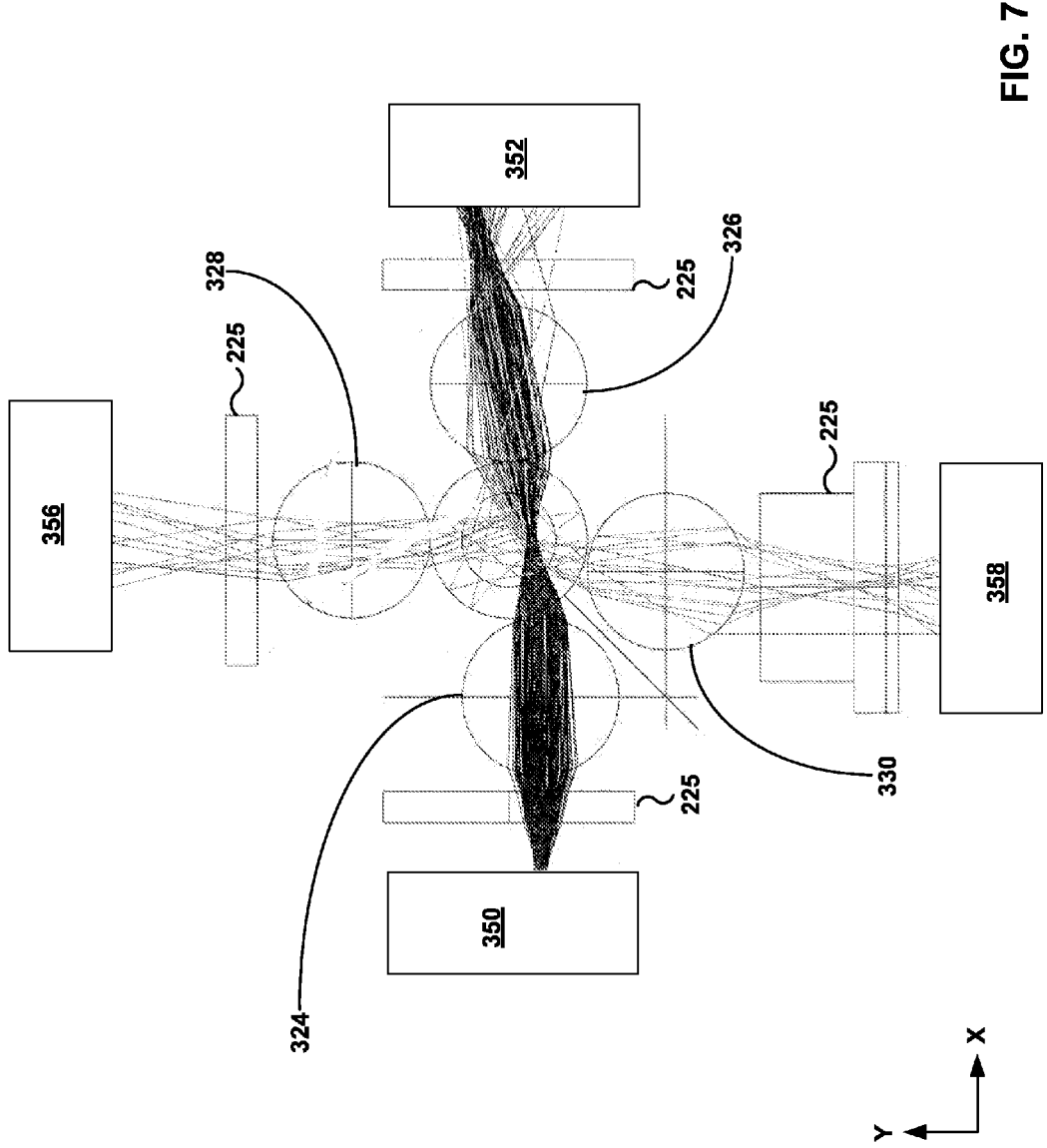
FIG. 7 is a cross-sectional drawing of an example alternative configuration of the optical sensor of FIG. 6.

FIG. 7 illustrates yet another example arrangement of optical sensor 300. Optical sensor 300 in FIG. 7 is the same as the optical sensor in FIG. 6 except that fourth optical window 330 and third optical detector 358 have been moved in the negative X-direction. In one example in which optical sensor 300 is arranged as illustrated in FIG. 7 (and where optical analysis area 314 is a quartz tube having a 3 mm internal diameter and a 5 mm external diameter, first optical window 224 is offset in the negative Y-direction by 1 mm, fourth optical window is offset in the negative X-direction 1 mm, and third optical detector 358 is offset in the negative X-direction 2.5 mm), it is expected that third optical detector 358 will provide a fluorescence signal of 22.2 µW when tested under similar conditions as discussed above with respect to the example in connection with FIG. 6. This is higher than when all components are symmetrical around optical analysis area 314 and when only first optical 324 is offset.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a non-transitory computer-readable medium, such as a computer-readable storage medium, containing instructions. Instructions embedded or encoded in a computer-readable storage medium may cause a programmable processor, or other processor, to perform the method, e.g., when the instructions are executed. Non-transitory computer readable storage media may include volatile and/or non-volatile memory forms including, e.g., random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

The invention claimed is:

1. An optical sensor comprising:
an optical emitter that is configured to direct light through an optical emitter window into a fluid sample;
a first optical detector that is configured to detect light emitted by the optical emitter and transmitted through the fluid sample;
a second optical detector that is configured to detect light emitted by the optical emitter and scattered by the fluid sample;
a third optical detector that is configured to detect fluorescent emissions emitted by the fluid sample in response to the light emitted by the optical emitter;
an optical emission filter positioned between the optical emitter and the fluid sample;
a first optical detection filter positioned between the first optical detector and the fluid sample;
a second optical detection filter positioned between the second optical detector and the fluid sample; and
a third optical detection filter positioned between the third optical detector and the fluid sample, wherein the optical emission filter, the first optical detection filter, and the second optical detection filter are each configured to filter out the same wavelengths of light so that substantially any light detected by the first optical detector and the second optical detector is light emitted from the optical emitter and passing through the fluid sample, and the optical emitter window is offset such that a geometric center of the optical emitter window is positioned closer to the third optical detector than the second optical detector.

2. The sensor of claim 1, wherein the third optical filter is configured to filter out substantially all the wavelengths of light emitted by the optical emitter and passing through the optical emission filter.

3. The sensor of claim 1, wherein the optical emission filter, the first optical detection filter, and the second optical detection filter are each configured to filter out wavelengths of light greater than approximately 300 nanometers.

4. The sensor of claim 1, further comprising a housing that defines an optical analysis area through which the fluid sample can travel for optical analysis, the housing including an optical emitter assembly that carries the optical emitter, a first optical detector assembly that carries the first optical detector, a second optical detector assembly that carries the second optical detector, and a third optical detector assembly that carries the third optical detector.

5. The sensor of claim 4, wherein the optical emitter window is positioned between the optical emitter and the optical analysis area, and the housing further comprises a first optical detector window positioned between the first optical detector and the optical analysis area, a second optical detector window positioned between the second optical detector and the optical analysis area, and a third optical detector window positioned between the third optical detector and the optical analysis area.

6. The sensor of claim 5, wherein the first optical detector window is positioned on an opposite side of the optical analysis area from the optical emitter window, the second optical detector window is positioned at an approximately 90 degree angle relative to the optical emitter window, and the third optical detector window is positioned on an opposite side of the optical analysis area from the second optical detector window.

7. The sensor of claim 5, wherein the optical analysis area comprises a tube that has an inner diameter and an outer diameter, and wherein the optical emitter window, the first optical detector window, the second optical detector window, and the third optical detector window each comprise a ball lens positioned to face the outer diameter of the tube.

8. The sensor of claim 7, wherein the tube defines a geometric center through which the fluid sample travels, and the optical emitter window is offset relative to the geometric center of the tube so that light emitted through the geometric center of the ball lens of the optical emitter window does not pass through the geometric center of the tube.

9. The sensor of claim 7, wherein the second optical detector window is positioned at an approximately 90 degree angle relative to the optical emitter window and the third optical detector window is positioned on an opposite side of the tube from the second optical detector window.

10. The sensor of claim 1, further comprising a temperature sensor, a pH sensor, and a conductivity sensor.

11. The sensor of claim 10, wherein electronics for the temperature sensor are positioned on a circuit board that contains one of the first, second, or third optical detectors, electronics for the pH sensor are on a circuit board that contains a different one of the first, second, or third optical detectors, and electronics for the conductivity sensor are on a circuit board that contains yet a different one of the first, second, or third optical detectors.

12. A method comprising:
emitting light into a fluid sample via an optical emitter;
detecting light emitted from the optical emitter and transmitted through the fluid sample via a first optical detector;
detecting light emitted from the optical emitter and scattered by the fluid sample via a second optical detector; and
detecting fluorescent emissions emitted by the fluid sample in response to light emitted by the optical emitter via a third optical detector,
wherein detecting light via the first optical detector and detecting light via the second optical detector further comprises filtering the light so that substantially any light detected by the first optical detector and the second optical detector is light emitted from the optical emitter and passing into the fluid sample, and
emitting light via the optical emitter comprises emitting light through an optical window so that light passing through a geometric center of the optical window is directed closer to the third optical detector than the second optical detector.

13. The method of claim 12, wherein detecting fluorescent emissions via the third optical detector further comprises filtering out substantially all wavelengths of light emitted by the optical emitter and passing into the fluid sample.

14. The method of claim 12, wherein detecting light via the first optical detector comprises detecting light on an opposite side of an optical analysis area from where the optical emitter is positioned, detecting light via the second optical detector comprises detecting light at an approximately 90 degree angle relative to where the optical emitter is positioned, and detecting fluorescent emissions via the third optical detector comprises detecting fluorescent emissions on an opposite side of the optical analysis area from where the second optical detector is positioned.

15. The method of claim 12, wherein emitting light via the optical emitter comprises emitting light through the optical emitter window so that light passing through a geometric center of the optical emitter window is not directed at a geometric center of an optical analysis area.

16. An optical sensor system comprising:
a housing that defines an optical analysis area through which a fluid sample travels for optical analysis, the housing including an optical emitter assembly that carries an optical emitter configured to direct light into the fluid sample, an optical emission filter positioned between the optical emitter and the optical analysis area, a first optical detector assembly that carries a first optical detector configured to detect light emitted by the optical emitter and transmitted through the fluid sample, a first optical detection filter positioned between the first optical detector and the optical analysis area, a second optical detector assembly that carries a second optical detector configured to detect light emitted by the optical emitter and scattered by the fluid sample, a second optical detection filter positioned between the second optical detector and the optical analysis area, a third optical detector assembly that carries a third optical detector configured to detect fluorescent emissions emitted by the fluid sample in response to the light emitted by the optical emitter, and a third optical detection filter positioned between the third optical detector and the optical analysis area, wherein the housing includes an optical emitter window positioned between the optical emitter and the optical analysis area, a first optical detector window positioned between the first optical detector and the optical analysis area, a second optical detector window positioned between the second optical detector and the optical analysis area, and a third optical detector window positioned between the third optical detector and the optical analysis area, the first optical detector window is positioned on an opposite side of the optical analysis area from the optical emitter window, the second optical detector window is positioned at an approximately 90 degree angle relative to the optical emitter window, and the third optical detector window is positioned on an opposite side of the optical analysis area from the second detector window, the optical emission filter, the first optical detection filter, and the second optical detection filter are each configured to filter out the same wavelengths of light so that substantially any light detected by the first optical detector and the second optical detector is light emitted from the optical emitter and passing through the optical analysis area, and the optical emitter window is offset so a geometric center of the optical emitter window is positioned closer to the third optical detector window than the second optical detector window.

17. The system of claim 16, wherein the third optical filter is configured to filter out substantially all the wavelengths of light emitted by the optical emitter and passing through the optical analysis area.

18. The system of claim 16, wherein the optical analysis area comprises a tube having an inner diameter and an outer diameter, and the optical emitter window, the first optical detection window, the second optical detection window, and the third optical detection window each comprise a ball lens positioned to face the outer diameter of the tube.

19. The system of claim 16, wherein the optical analysis area defines a geometric center through which the fluid sample travels, and the optical emitter window is offset relative to the geometric center of the optical analysis area so that light emitted through a geometric center of the optical emitter window is not directed to pass through the geometric center of the optical analysis area.

* * * * *